United States Patent [19]

Buchwalder

[11] Patent Number: 4,665,033

[45] Date of Patent: May 12, 1987

[54] PROCESS AND AN APPARATUS FOR CULTURING MICROORGANISMS IN A NUTRIENT SOLUTION

[75] Inventor: Gerard Buchwalder, Delemont, Switzerland

[73] Assignee: Zentrale Finanz- und Kommerz-Aktiengesellschaft, Vaduz, Liechtenstein

[21] Appl. No.: 588,962

[22] Filed: Mar. 13, 1984

[30] Foreign Application Priority Data

Mar. 16, 1983 [EP] European Pat. Off. .................. PCT/EP83/00079

[51] Int. Cl.$^4$ .................. G11C 17/00; C10J 1/18; B01D 1/00; C12N 5/00; C12N 1/00; C12M 3/02; C12C 1/00

[52] U.S. Cl. .................................... 435/243; 435/240; 435/241; 435/283; 435/284; 435/286; 435/287; 435/309; 435/313; 435/315; 435/818; 261/87; 261/122; 261/123; 210/218; 210/220; 366/101

[58] Field of Search .............. 435/240, 241, 283, 284, 435/286, 287, 309, 313, 315, 243, 818; 261/87, 123, 122; 210/218, 220; 366/101

[56] References Cited

U.S. PATENT DOCUMENTS

| 3,764,014 | 10/1973 | Stem et al. | 210/220 |
|---|---|---|---|
| 4,017,565 | 4/1977 | Müller | 210/36 R |
| 4,025,394 | 5/1977 | Young | 435/198 |
| 4,079,008 | 3/1978 | Neumann | 210/194 |
| 4,208,483 | 6/1980 | Lee | 435/284 |
| 4,259,449 | 3/1981 | Katinger et al. | 435/241 |
| 4,290,885 | 9/1981 | Kwak | 210/197 |
| 4,311,798 | 1/1982 | Katinger et al. | 435/241 |
| 4,374,730 | 2/1983 | Braha et al. | 210/608 |

FOREIGN PATENT DOCUMENTS

| 4409022 | 5/1982 | European Pat. Off. | 435/286 |
|---|---|---|---|
| 181039 | 4/1966 | U.S.S.R. | |

OTHER PUBLICATIONS

Van Wezel et al, *Proc. Biochem.*, Mar. 1978, pp. 6–8.

*Primary Examiner*—Thomas G. Wiseman
*Assistant Examiner*—Robin Lyn Teskin
*Attorney, Agent, or Firm*—Birch, Stewart, Kolasch & Birch

[57] ABSTRACT

In a process for culturing microorganisms in a sealed vessel, the nutrient solution is circulated directionally and the microorganisms are kept in suspension in the moving directional flow. The oxygen-containing gas for aeration of the nutrient solution is run into the solution in such a way that it has a component of motion normal to the direction of flow of the nutrient solution.

22 Claims, 3 Drawing Figures

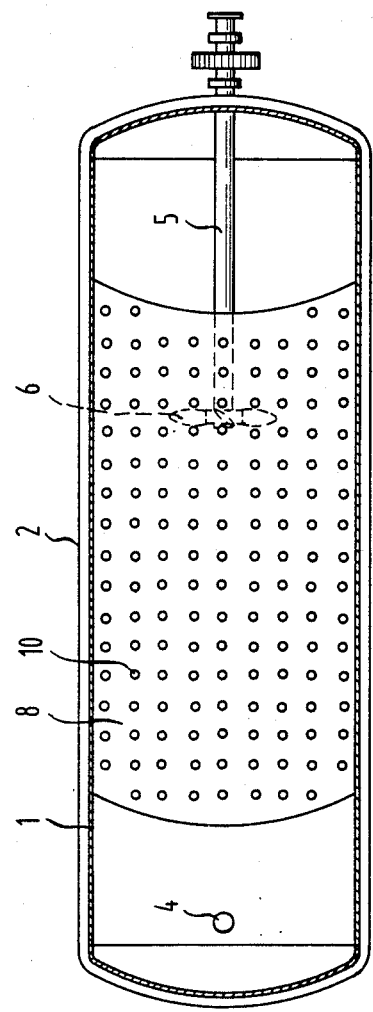
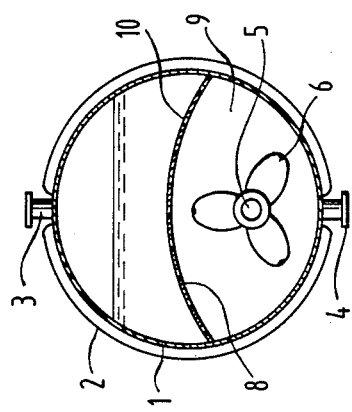

PROCESS AND AN APPARATUS FOR CULTURING MICROORGANISMS IN A NUTRIENT SOLUTION

BACKGROUND OF THE INVENTION

The present invention relates to the culture of microorganisms in a sealed vessel in which they are kept in suspension in nutrient substrate solution that is aerated with oxygen-containing gas.

The submerged culture microorganisms are generally kept in suspension in a liquid nutrient solution in which the parameters on which growth is dependent, such as the pH value, the oxygen concentration and others, are carefully controlled. For the optimum supply of the microorganisms suspended in the nutrient solution with substances essential for growth, such as a source of carbon, salts, vitamins, trace elements and oxygen and for the removal of the products of microbiological metabolism, it is necessary to maintain certain specific culture conditions, that is to say an intensive mixing of the nutrient substrate solution in order to obtain a homogeneous distribution of the phases, a high gas-liquid mass exchange rate and a good distribution of the gas phase. Furthermore, there has to be an efficient way of conducting away the heat produced. In this connection the wording homogeneous distribution is used in the sense of not only homogenization (the normal sense of the wording) of the dissolved substrate components in the vehicle phase (normally water), but furthermore it is used in the sense of a complete suspension of each and every microorganism in the
nutrient solution.

In connection with the culture of microorganisms in vessels certain troubling conditions are likely in the day-to-day operation of the plant inasfar as the microorganisms frequently have the tendency of building up densely packed layers on the wall of the reactor, this causing on the one hand an improverishment of the nutrient substrate solution with respect to active microorganisms and on the other hand a loss in productivity or drop in product quality, because the microorganisms forming the layer on the wall will only get a limited supply of nutrients. Acting on the notion that flow conditions in the culture vessel have been the main cause of decreased growth of the microorganisms, attempts have been made in the past to overcome this undesired effect by producing a higher degree of turbulence in the culture vessel. Although it has in fact been possible for good effects to be produced when working on a small scale, that is to say under lab conditions with a 5 to 200 liter vessel, inasfar as there was then much less wall-adherent growth, the scaling up of the process with turbulent nutrient flow to the size of vessels normally used in regular production plant, that is to say with a capacity of 10,000 to 50,000 liters, has not been possible without serious shortcomings. This is because on the one hand the power necessary for the agitating or stirring effect went up in proportion to the volume of the vessel and, on the other hand there was some trouble experienced in conducting away the heat produced by agitation and the sizeable amount of heat of reaction caused by aerobic bioprocesses, if the plant was to be run at a low culture temperature. Furthermore, attempts have been made at putting an end to the formation of dead zones in which there is no or hardly any mixing effect in the nutrient substrate solution by causing a carefully controlled and defined circulation of the suspension throughout the volume of the vessel. However, on testing under working conditions there was seen to be the shortcoming that a high specific drive power was needed and that the gas phase was not homogeneously divided up and distributed so that there was less growth of the microorganisms.

In the prior art, microorganisms have furthermore been aerobically cultured in a fermenter designed as a so-called toroidal reactor. Such a fermenter was made up of a hollow torus in which the nutrient substrate solution was kept circulating by a tangential agitator and gas was supplied thereto. Although the specific drive power needed for operation of this fermenter was relatively low, trouble was caused by premature segregaton of gas so that there was a tendency for the supply of oxygen not to be high enough.

SUMMARY OF THE PRESENT INVENTION

One purpose of the present invention is that of designing a process and an apparatus for the culture of microorganisms that put and end to the danger of the microorganisms adhering to the vessel wall.

A further purpose of the process and apparatus of the present invention is to make certain that there is high enough rate of oxygen supply to the microorganisms.

As seen from a further aspect, the present invention is to make possible such processes and apparatus without any limit to the size of culture vessel.

The process of the present invention for the submerged culture of microorganisms in a sealed container, in which they are kept in suspension and in which an oxygen-containing gas is pumped in to the culture, is characterized in that a directional flow of the nutrient subtrate solution is produced, the microorganisms being kept in suspension in the said directional flow and the gas run into and distributed in the nutrient substrate solution has a component of motion that is normal to the direction of flow of the said nutrient substrate solution.

A plant for running the process of the invention may be said to be characterized by the use of a vessel longer than it is wide and so placed that its longer axis is horizontal, by an agitating means and by level liquid guide means placed in the nutrient substrate solution in the vessel and causing the flow as produced by said agitating means to become directional.

By using the present invention it becomes possible, more specially when the flow of the nutrient substrate solution is a circulatory one, to be certain that there is materially no adhesion or sticking of the microorganisms to the wall of the vessel while the specific power is kept down to a low level. An even and materially turbulence-free circulation of suspension is kept up throughout all parts of the vessel or tank. The bubbles of the oxygen-containing gas pumped into the vessel are kept on the move by the upthrust in a direction normal to the direction of liquid flow and this is responsible for there being a high volumetric transition coefficient. There is furthermore the very useful effect that the process may be run in any size of vessel, that is to say there is no upper limit to the vessel size.

In keeping with a preferred further development of the invention the flow guide means has a perforated plate, which as seen in an end-on view of the vessel is curved upwards. Such a form of guide means is at one and the same time simple and highly efficient.

As part of a still further outgrowth of the invention, the agitator is in the form of a propeller with a hollow driving shaft through which the oxygen containing gas is supplied so that there is a specially fine division of the gas flow. Furthermore the size of the gas bubbles may be controlled.

Further useful developments of the invention will be seen from the claims.

An account will now be given of one working example of the invention to be seen in the figures herein.

BRIEF DESCRIPTION OF THE DRAWINGS

FIG. 2 is a diagrammatic top plan view and part section of the apparatus of the
invention as seen in FIG. 1.

FIG. 3 is diagrammatic end- view and part section of the apparatus in
keeping with the present invention.

Figure 1:
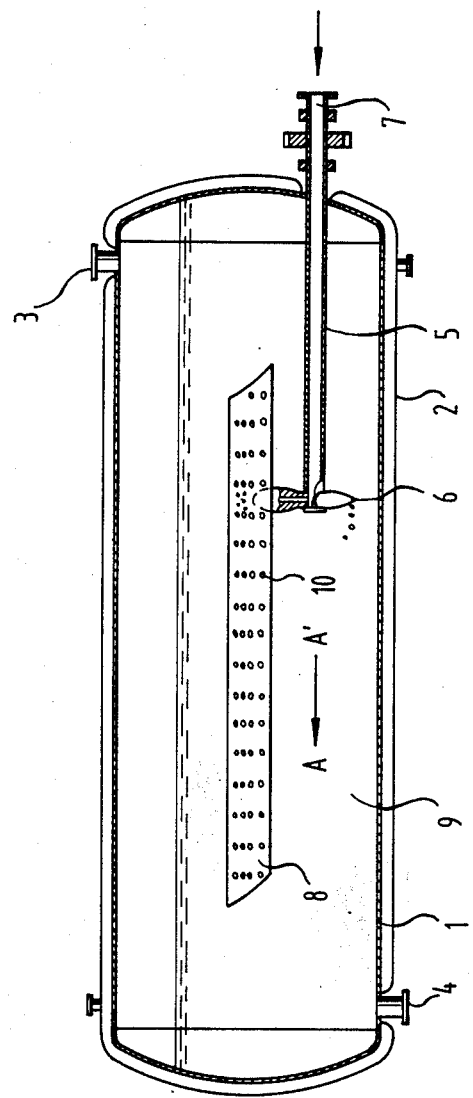
FIG. 1 is a diagrammatic side view and part section of one form of
apparatus in keeping with the present invention.

DETAILED DESCRIPTION OF THE INVENTION.

The apparatus of FIG. 1 has vessel or tank 1 made of stainless steel for example and placed so that its longer axis is on the level. It is fully within a heat exchanger jacket 2. The vessel 1 has a cylindrical side wall and dished end walls or plates so formed, if desired, that their generatrices are in the form of flattened circular or elliptical curves. The vessel 1 is filled through an inlet connector 3 with nutrient substrate solution that is seeded with microorganisms. There is a further outlet connector 4 for removing the fermentation broth after fermentation has been completed. There is a propeller 6 for acting as a hollow stirring or agitating means. The hollow driving shaft 5 of the propeller 6 is used for pumping oxygen-containing gas into the nutrient substrate solution. The outer end of the shaft 6 is joined up with a gas connector 7. In the nutrient substrate solution the propeller 6 is placed under a flow guide means that in the present case is in the form of a perforated plate 8 or baffle. As the solution comes from the propeller, the direction of the distributed gas in the nutrient substrate solution 9 is initially as marked at A', A. The current of gas bubbles moving upwards, that is to say with a component of motion that is normal to the direction of flow of the nutrient substrate solution 9, makes its way in part through the perforated plate 8 or baffle so that there is a further division or atomisation of the bubbles and the gas current then goes through a further part of the nutrient substrate solution, before the rest of the gas is aspirated out of the system by way of the connector 3.

In FIG. 2 the position of the perforated plate 8 with its holes 10 or perforations is shown. This FIG. 2 furthermore makes clear the free cross sections or passageways within the vessel, in which the nutrient substrate solution 9 is circulated. These passgeways are produced because the perforated plate 8 is only fixed in place on the side walls of the vessel and comes to an end some distance short of the two end walls of the vessel so that the said passageways are produced for the flow of the nutrient substrate solution around the ends of the plate 8. At the left hand end of the vessel the circulating nutrient substrate solution makes its way upwards from a position under the perforated plate 8 while at the right hand end of the perforated plate it goes downwards from the level over the perforated plate 8 into the part of the vessel at a lower level than the plate 8. The perforated plate 8 is fixed at such a level to the side wall of the vessel 1 that the flow cross sections for the circulating flow of the nutrient substrate solution under and over the perforated plate 8 are of the same size. It will be clear from the end-on view of FIG. 3 how the perforated plate 8 is fixed to the side walls of the vessel 1 and is upwardly curved or vaulted.

The diameter of the holes in the perforated plate 8 is in a range of 0.5 mm to 5 mm with a preferred size of 2 mm, such holes making up 15% to 40% and more specially 23% of the area of the perforated plate.

The useful effects of the apparatus in keeping with the invention for culturing microorganisms will be seen from the examples now to be given.

EXAMPLE 1

In the lab, a seeded culture of *Streptomyces aureofaciens* may be grown under optimum conditions in a 5 liter fermenter with an agitating turbine and an aeration rate of 1.5 volume units of air per volume unit of liquid per minute to give a maximum yield of 18 grams of chlortetracycline per liter of nutrient substrate solution.

This culturing operation with the same microorganism was scaled up by running it in a 3000 liter turbine agitator fermenter with aeration system in keeping with the DECHEMA operation standard (DECHEMA standing for Deutsche Gesellschaft fuer Chemisches Apparatewesen eV), with a rate of aeration being 1 volume unit of air per volume unit of liquid per minute and a specific agitation power of 1.5 watts per liter, the maximum yield of chlortetracycline per liter of nutrient substrate solution being 12 grams. Such a 3000 liter fermenter in keeping with the said DECHEMA standard of operation was a cylindrical tank with its cylinder axis upright. The end walls were elliptical and the length to diameter ration was 3.3.

After the fermentation had been completed, the apparatus was checked and it was noted that there was heavy growth of the microorganism at the flow baffles.

EXAMPLE 2

In this case an apparatus in keeping with the invention was used that was in the form of a cylindrical vessel with a liquid volume of 3000 liters as in FIG. 1 herein with elliptical ends and with the longer axis on the level. The length to diameter ratio was 3.3. The specific agitation power was 1 watt per liter of nutrient substrate solution and the aeration rate was 1 volume unit per volume unit of liquid per minute. The nutrient substrate solution was seeded with the same culture of *S. aureofaciens* as in Example 1. Fermentation was ended after the same time as in the lab scale process of Example 1. The yield of chlortetracycline was 18 grams a liter of the nutrient substrate solution. There was no growth of organisms adhering to the vessel wall.

The level guide or baffle means used in Example 2 was a perforated plate with a perforation area of 23% and a perforation diameter of 2 mm.

What is claimed is:

1. Apparatus for culturing microorganisms in a nutrient substrate solution, comprising:
   a horizontally arranged elongate fermenting vessel which is longer in the horizontal direction than it is in the vertical direction;
   horizontally arranged flow guide means for guiding the flow of nutrient solution in said vessel, said flow guide means comprising an elongate perforated plate having first and second longitudinal ends which are spaced from the respective longitudinal ends of the fermenting vessel;

circulating means for agitating and circulating nutrient substrate solution over and under said perforated plate and around said longitudinal ends of said perforated plate; and means for introducing oxygen-containing gas bubbles into the nutrient solution under said flow guide means whereby said bubbles rise in said nutrient solution and pass through perforations in said perforated plate.

2. The apparatus of claim 1, wherein the sides of said perforated plate are secured to said fermentation vessel.

3. The apparatus of claim 2, wherein the longitudinal center of said perforated plate is higher than the sides of said perforated plate.

4. The apparatus of claim 2, wherein perforations in said plate have a diameter between 0.5 and 5 mm.

5. The apparatus of claim 2, wherein perforations in said plate take up between 15% and 40% of the area of the plate.

6. Apparatus for culturing microorganisms in a nutrient substrate solution, comprising:

a fermenting vessel for nutrient substrate solution, said vessel being longer than it is high and being so placed that its longer axis is level, said vessel having a side wall running along and temporarily parallel to the longer axis of the vessel and end walls at front and back ends of the said side wall;

horizontally arranged flow guide means for guiding the flow of nutrient substrate solution in said vessel, said flow guide means comprising a perforated plate fixed to said side wall so that the ends thereof are spaced from said end walls for forming passageways between said front and back end walls and the ends of the perforated plate for permitting a circulation flow of said nutrient substrate solution over and under the said perforated plate;

circulating means for agitating and circulating nutrient solution in said vessel, said circulating means comprising an agitating propellor placed at a lower level than the said perforated plate for producing said circulation flow; and gas blowing means for blowing oxygen-containing gas through a hollow driving shaft of said agitating propellor to said nutrient substrate solution whereby oxygen-containing gas is distributed in nutrient substrate solution having a component of motion that is normal to the direction of circulation flow of the nutrient substrate solution.

7. The apparatus of claim 6, wherein the cross sections of said vessel under and over said flow guide means are of equal size.

8. The apparatus of claim 6, wherein the end walls of the vessel are outwardly curved.

9. The apparatus of claim 6, wherein said perforated plate is upwardly curved.

10. The apparatus of claim 9, wherein perforations in said plate are round and have a diameter between 0.5 and 5 mm.

11. The apparatus of claim 10, wherein said perforations have a diameter of about 2 mm.

12. The apparatus of claim 10, wherein perforations in said perforated plate take up between 15% and 40% of the area of the plate.

13. The apparatus of claim 10, wherein perforations in said perforated plate take up about 23% of the area of the plate.

14. The apparatus of claim 6, wherein said perforations are equally spaced from each other.

15. Apparatus for culturing microorganisms in a nutrient substrate solution, comprising:

a horizontally arranged elongate fermenting vessel which is longer in the horizontal direction than it is in the vertical direction having first and second longitudinal ends;

horizontally arranged flow guide means for guiding the flow of nutrient solution in said vessel, said flow guide means comprising an elongate perforated plate having first and second longitudinal ends which are spaced respectively from the first and second longitudinal ends of the fermenting vessel;

circulating means for circulating nutrient substrate solution under said perforated plate from said first longitudinal end of said perforated plate to said second longitudinal end of said perforated plate, around said second longitudinal end of said perforated plate, over said perforated plate from said second end thereof to said first end thereof and around said first end of said perforated plate; and means for introducing oxygen-containing gas bubbles into the nutrient solution under said perforated plate and near the first end thereof whereby said bubbles rise in said nutrient solution and pass through perforations in said perforated plate.

16. The apparatus of claim 15, wherein the longitudinal center of said perforated plate is higher than the sides of said perforated plate.

17. The apparatus of claim 15, wherein said first and second longitudinal ends of said vessel are outwardly curved.

18. The apparatus of claim 15, wherein said circulating means is located under said first end of said perforated plate.

19. The apparatus of claim 15, wherein said fermenting vessel is cylindrical in shape.

20. The apparatus of claim 17, wherein said fermenting vessel is cylindrical in shape and a smooth surface is formed between said cylindrical fermenting vessel and said outwardly curved ends.

21. A process for the submerged culture of aerobic microorganisms, comprising the steps of:

suspending aerobic microorganisms in a nutrient substrate solution;

introducing said nutrient substrate solution containing aerobic microorganisms into a horizontally arranged fermenting vessel which is longer than it is high and which has a horizontally arranged flow guide means disposed therein between the top and bottom of said fermentation vessel, said flow guide means having first and second ends spaced from respective first and second ends of said vessel and having gas passageways therein;

circulating said nutrient medium in a circular path around said first and second ends of said flow guide means; and introducing oxygen-containing gas into said vessel underneath of said flow guide means wherein gas bubbles rise through said gas passageways in said flow guide means.

22. The process of claim 21, wherein said aerobic microorganisms are bacteria.

* * * * *